(12) United States Patent
Zubarev et al.

(10) Patent No.: US 7,476,853 B2
(45) Date of Patent: Jan. 13, 2009

(54) ION FRAGMENTATION BY REACTION WITH NEUTRAL PARTICLES

(75) Inventors: Roman Zubarev, Sigtuna (SE); Alexander Misharin, Uppsala (SE); Oleg Silivra, Uppsala (SE); Frank Kjeldsen, Uppsala (SE)

(73) Assignee: Bruker Daltonik GmbH, Bremen (DE)

( * ) Notice: Subject to any disclaimer, the term of this patent is extended or adjusted under 35 U.S.C. 154(b) by 347 days.

(21) Appl. No.: 11/349,551

(22) Filed: Feb. 7, 2006

(65) Prior Publication Data

US 2006/0192100 A1  Aug. 31, 2006

(30) Foreign Application Priority Data

Feb. 7, 2005 (DE) .................. 10 2005 005 743

(51) Int. Cl.
*B01D 59/44* (2006.01)
*H01J 49/00* (2006.01)

(52) U.S. Cl. .................. 250/292; 250/281; 250/282; 250/287; 250/288; 250/423 P; 250/461.1; 250/910; 435/6; 435/7; 435/91.2; 435/91.1; 435/320; 435/325; 702/20; 703/11; 536/24.3; 536/25.3; 536/23.1; 436/63; 436/106; 436/21; 424/178.1; 356/301

(58) Field of Classification Search .................. 250/292, 250/281, 282, 287, 288, 423 P, 461.1, 910; 435/6, 7.1, 91.2, 91.1, 320.1, 325; 702/20; 703/11; 536/24.3, 25.3, 23.1; 436/501, 63, 436/106, 21; 424/178.1; 356/301

See application file for complete search history.

(56) References Cited

U.S. PATENT DOCUMENTS 4,736,101 A    4/1988  Syka et al.
2002/0102572 A1*  8/2002  Crooke et al. .................. 435/6

FOREIGN PATENT DOCUMENTS

DE   100 58 706 C1   11/2000
EP   0202943 A2      5/1986
EP   0409362 A2      5/1986
EP   0350159 A1      6/1989
EP   1598850 A2      5/2005

OTHER PUBLICATIONS

Hager, James W., "A new linear ion trap mass spectrometer", Rapid Communications IN mass Spectrometry, vol. 16, John Wiley & Sons, Ltd., pp. 512-526, 2002.
Syka, et al., "Peptide and protein sequence analysis by electron transfer dissociation mass spectrometry", PNAS, vol. 101, No. 26, pp. 9528-9533, 2004.

* cited by examiner

*Primary Examiner*—Jack I Berman
*Assistant Examiner*—Meenakshi S Sahu
(74) *Attorney, Agent, or Firm*—Law Offices of Paul E. Kudirka

(57) ABSTRACT

The invention relates to a method and apparatus for the fragmentation of large molecules, especially biopolymers. The invention consists in reacting analyte ions with excited or radical neutral particles, whereby, at least in the case of bombardment of analyte ions with helium atoms from an FAB generator, a new type of fragmentation occurs which strongly resembles fragmentation by electron capture (ECD). The reactions may be performed in magnetic ion traps (ion cyclotron resonance cells, ICR), in RF ion traps according to Wolfgang Paul, in RF ion guides, or in free beams of analyte ions or neutral particles.

24 Claims, 5 Drawing Sheets

ION FRAGMENTATION BY REACTION WITH NEUTRAL PARTICLES

FIELD OF THE INVENTION

The invention relates to a method and apparatus for the fragmentation of large molecules, especially biopolymers.

BACKGROUND OF THE INVENTION

The aim of human proteomics is to identify all the proteins of the human body, to determine their ever-changing structures and modifications, to identify their interaction partners and to find out the partners and type of interactions with other proteins. The 22,000 genes which have been found in the human genome generate a much larger number of different types of proteins (100 to 1000 times more) as a result of mutations, posttransscriptional and posttranslational modifications of the proteins. The task of human proteomics is therefore immense. Further tasks are waiting in animal proteomics and plant proteomics. In the end, success in researching these building blocks of our life will depend on the development of effective tools for identifying protein structures and their modifications.

Tandem mass spectrometry (MS/MS) is one of most useful tools in proteomics because of its high detection power (femtomoles and lower) and its high specificity. The conventional MS/MS method of protein characterization consists in enzymatic digestion of the protein and subsequent fragmentation of the digest peptides in the mass spectrometer by collisions with a collision gas. (Definition: peptides are small proteins with up to about 30 or 40 amino acids; digest peptides are formed from larger proteins by enzymatic digestion, for example by trypsin). The masses of the fragment ions and the molecular ion are then entered into a search engine, which compares the measured fragmentation pattern with theoretical fragmentation patterns of the virtual digest peptides of all the proteins in a protein sequence database. The success of this method depends on how many fragment ions are formed from the digest peptide ion and how characteristic these fragment ions of a given digest peptide are.

The customary fragmentation technique is collisionally induced fragmentation (CID=collision induced dissociation, also often called CAD=collisionally activated dissociation). The peptide ions are accelerated to kinetic energies of between 20 and 4000 electronvolts and collide with molecules of neutral gas, thereby exciting internal bonding systems to oscillations. CID preferably splits the so-called peptide bonds (C—N bonds in the central chain of amino acids) thereby forming so-called N-terminal B fragments and C-terminal Y fragments. The disadvantages of this fragmentation are, firstly, losses of side chains which are easily split off—these groups occur in many posttranslational modifications (for example phosphorylations and sulfations)—and, secondly, the incomplete fragmentations which frequently occur.

In reality, the information on the protein transmitted to the database search engines in the form of MS/MS spectra is rarely complete, and therefore false identifications cannot be ruled out. In fact, they occur rather frequently because the databases contain only a minute fraction of all actually occurring proteins. Even if the genome has been completely decoded, particularly all mutational forms and modifications are lacking in the data base. False identifications and incorrect structural information are a serious problem of present day proteomics.

To avoid false identifications and incorrect structural information, independent (so-called "orthogonal") and preferably also gentle types of fragmentation must be available. Methods which are orthogonal to each other provide confirmatory information via other, independent means. These orthogonal fragmentation methods can be drawn on to confirm the identifications and correct the structural information. A good candidate for a type of fragmentation orthogonal to collisionally induced fragmentation CID is electron capture dissociation (ECD), which splits N—$C_a$ bonds of the amino acid chain and generates N-terminal C fragments and C-terminal Z fragments without losing labile groups in the process. The mass difference between B and C ions of the same type is +17 atomic mass units (Daltons), and the difference between Z and Y ions is −16 Daltons. These mass differences, which must occur between the independent measurements, given the correct identification, can make the identification more certain. Applying a combination of CID and ECD increases the certainty of the identification by factors of between 20 and 100.

Up to now, fragmentation by electron capture ECD could only be used routinely in expensive ion cyclotron resonance mass spectrometers ICR-MS (also called Fourier transform mass spectrometer FTMS). The prerequisite for this fragmentation method is that doubly charged ions of the analytical substance (termed analyte substance below) are available.

A further method of fragmentation has recently been published which also is orthogonal to collisionally induced fragmentation CID: The fragmentation of multiply charged positive ions by reactions with suitable negative ions by electron transfer is called "electron transfer dissociation" or ETD, described by J. E. P. Syka, J. J. Coon, M. J. Schroeder, J. Shabanowitz and D. F., Hunt in the paper "Peptide and protein sequence analysis by electron transfer dissociation mass spectrometry", Proc. Natl. Acad. Sci. USA 2004, 101, 9528-9533. These reactions can take place in RF ion traps, which means both linear ion traps made of rod electrodes and three-dimensional ion traps made of ring electrodes and end cap electrodes. But to obtain high yields of fragment ions, it is necessary to start with triply charged ions. For this reason the method has its limitations, because precisely for digest peptides—which are by far the most interesting biomolecules—triply charged ions can only be produced with a very limited yield. The fact that it is necessary to begin with triply charged analyte ions reduces the detection power of the method with ETD by factors of between 10 and 20.

A commonly used way of ionizing large biomolecules is to use electrospray ionization (ESI), which ionizes ions at atmospheric pressure outside the mass spectrometer. These ions are then introduced into the vacuum of the mass spectrometer, and from there into the ion trap by means of inlet systems of a type which has already been described.

This type of ionization generates hardly any fragment ions. The ions are mostly those of the analyte molecule. Electrospray ionization does, however, produce multiply charged analyte ions. In the case of peptides, the doubly charged ions are the most prevalent ions in around 85 to 90 percent of cases. The triply charged ions generally represent only a few percent of all the ions formed. For lighter peptides, the singly charged ions are the most prevalent, the doubly charged ones the second most prevalent. The lack of almost any fragmentation of the analyte ions created during the ionization process limits the information from the mass spectrum to the molecular weight; there is no information concerning internal molecular structures which can be used for further identification of the substance present. This information can only be obtained by the above-described acquisition of fragment ion spectra in tandem mass spectrometers.

Owing to the high prices of Fourier transform mass spectrometers (FTMS) it would be desirable for fragmentation methods which are complementary and orthogonal to collisionally induced fragmentation CID, such as electron capture dissociation ECD, to also be carried out in simpler, smaller and less expensive mass spectrometers, for example in quadrupole ion trap mass spectrometers operated with RF voltages. Until now, the fragmentation in quadrupole ion traps has been exclusively carried out using collisionally induced fragmentation CID. For fragmentation by electron capture ECD, on the other hand, the kinetic energy of the electrons must be very low, as otherwise no capture can take place. In practice one supplies electrons with an energy just above the thermal energy. This works very well in the very strong magnetic fields of the Fourier transform mass spectrometer, but not in electric RF ion traps. It has not yet proven possible, neither in three-dimensional nor in linear ion traps, to fragment the ions by electron capture and obtain a high enough yield. The disrupting factor here is the fact that there is practically always a high electric field strength, which makes it difficult, if not impossible, for low-energy electrons to enter (in spite of patents in this fields, see J. Franzen DE 100 58 706 C1; or R. Zubarev et al. U.S. Pat. No. 6,800,851 B1).

Ion traps according to Wolfgang Paul normally comprise a ring electrode and two end cap electrodes, the ring electrode usually being supplied with the storage RF voltage. These ion traps are also called three-dimensional ion traps ("3D ion traps"). It is also possible to use four-rod quadrupole filters according to Paul as ion traps if both ends of the rod system are supplied with ion-repelling potentials through diaphragms. These so-called "linear quadrupole ion traps", or "linear ion traps" for short, are easier to fill with ions, and with slightly more ions than the "three-dimensional ion traps". In the interior of the ion trap, ions can be stored in the quadrupole RF field. Linear ion traps are also often called "two-dimensional ion traps" or "2D ion traps".

Both three-dimensional and linear ion traps can also be employed as ion analyzers by using resonant excitation to eject the ions selectively according to mass and then measuring them as ion currents. The ions can be mass-selectively ejected from the linear quadrupole ion traps either radially through slits in at least one of the long electrodes (U.S. Pat. No. 5,420,425, M. E. Bier and J. E. Syka, which corresponds to EP 0 684 628 A1), or axially by means of coupling processes in the inhomogeneous end field of the rod system ("A new linear ion trap mass spectrometer", J. W. Hager, Rapid Commun. Mass Spectrom. 2002, 16, 512-526). The mass-selectively ejected ions are measured by a detection unit, for example a secondary-electron multiplier, and then the measurements can be processed to a mass spectrum.

Ion trap mass spectrometers have properties which make them of interest for use in many types of analyses. In particular, selected ion species (so-called "parent ions") can be isolated and fragmented in the ion trap. The isolation consists in ejecting all undesired ions from the ion trap by resonant excitation and only leaving the desired analyte ions in the ion trap. The fragmentation occurs in a slightly different way to the fragmentation by acceleration of the analyte ions described above. By exciting their oscillations, the analyte ions are forced to undergo a large number of individual collisions with the collision gas, thereby absorbing very small portions of energy until finally a fragmentation occurs. Both this type of fragmentation and the collisionally induced fragmentation after acceleration provide fragment ions of the B and Y series. The spectra of these fragment ions are also called "daughter ion spectra" of the respective parent ions. In ion traps, "granddaughter ion spectra" can also be measured as fragment ion spectra of selected daughter ions.

SUMMARY OF THE INVENTION

The invention provides methods and devices for the fragmentation of analyte ions by reactions with highly excited or radical neutral particles. The reactions can be started either by bombardment of a cloud of analyte ions with a beam of excited or radical neutral particles, or by bombardment of a collection of such neutral particles by a beam of analyte ions. In the following we will assume that the analyte ions are produced from peptides or proteins, but other types of biomolecules should not be excluded.

The invention involves reacting multiply charged analyte ions with excited or radical neutral particles, whereby, at least in the case of bombardment of analyte ions with helium atoms from an FAB (FAB=fast atom bombardment) generator, a new type of fragmentation occurs which strongly resembles fragmentation by electron capture (ECD). The reactions may be performed in magnetic ion traps (ion cyclotron resonance cells, ICR), in RF ion traps according to Wolfgang Paul, in RF ion guides, or in free beams of analyte ions or neutral particles.

In the case of the bombardment of analyte ions with highly excited neutral particles it is preferable to start with doubly charged analyte ions generated predominantly by electrospray ionization, for instance from peptide molecules; higher charge states can also be used where necessary, for example with heavier proteins. The beam of excited neutral particles is preferably generated in a conventional FAB generator. Noble gas atoms are usually used for this, preferably helium atoms, but other types of atoms or molecules can also be used as the neutral particles of the beam.

In case of reactions with radical neutral particles, preferably with hydrogen radicals, it is even possible to start with singly charged analyte ions, as for instance produced by matrix-assisted laser desorption (MALDI). A beam of hydrogen radicals can be generated by commercially available generators; they are usually used for cleaning of wafers and chips from pollutions and oxides in electro-technical companies. Hydrogen radicals, for instance hydrogen atoms "in statu nascendi", are extraordinarily reactive. Hydrogen radicals can be produced thermally or in microwave plasmas.

The cloud of analyte ions can move through an ion guide, or it can be made available at rest in an ion trap. The ion trap can be a magnetic or an RF quadrupole ion trap of a linear or three-dimensional type. It is one of the advantages of the method that the respective prevailing electric or magnetic fields do not at all interfere with the beam of neutral particles. When using a beam of helium atoms from an FAB generator or a beam of hydrogen radicals, the fragment ion spectra surprisingly resemble those measured with electron capture dissociation ECD. The yield of fragment ions is relatively high, about as high as the yield of electron capture ECD in ICR mass spectrometers (possibly even higher).

The invention also comprises mass spectrometers with generators to produce either a beam of highly excited neutral particles or neutral radicals and either an ion trap to store analyte ions or an ion guide to transfer the analyte ions from an ion source to an ion analyzer, whereby the beam of neutral particles or radicals can be directed into the ion trap or into the ion guide. Also mass spectrometers can be provided with a chamber for the production of highly excited neutral particles or radical neutrals through which a beam of analyte ions can be directed.

BRIEF DESCRIPTION OF THE DRAWINGS

The above and further advantages of the invention may be better understood by referring to the following description in conjunction with the accompanying drawings in which.

For comparison.

For comparison.

For comparison.

DETAILED DESCRIPTION

Figure 1:
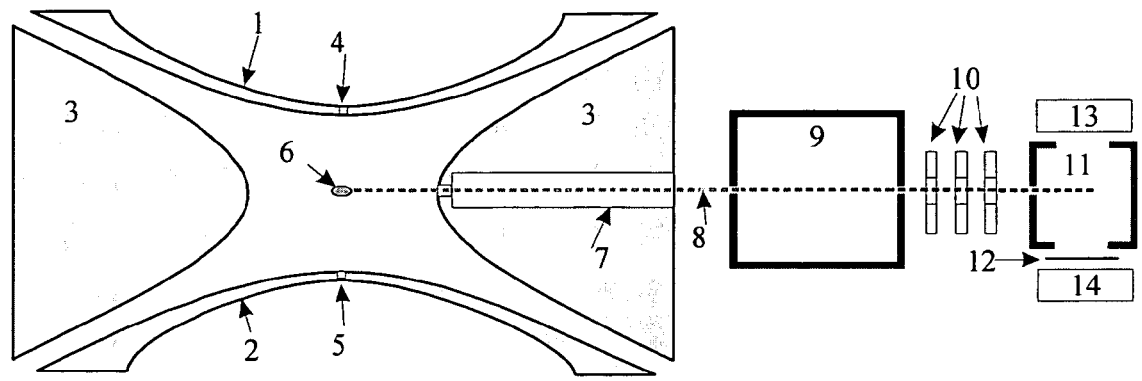
FIG. 1 schematically illustrates an ion trap with two end cap electrodes (1, 2) and a ring electrode (3). A beam of neutral particles (8) impinges on the stored cloud (6) of analyte ions via a hole (7) in the ring electrode (3). The beam of neutral particles (8) is produced in an FAB generator (9-14). In its electron collision chamber (11), electrons from a thermionic cathode (12), guided by a magnetic field between the magnets (13) and (14), initially generate ions for an ion beam, which accelerates as a result of potentials between electron collision chamber (11) and lens system (10) and is focused by the lens system (10). The ions are discharged in the charge reversal chamber (9) by charge exchange, and then form the beam (8) of neutral particles.

A particularly favorable embodiment of a method and apparatus are described with the help of FIG. 1. Analyte ions are stored as a cloud (6) in an ion trap made of two hyperboloidal end cap electrodes (1) and (2) and a hyperboloidal ring electrode (3). An RF voltage of a few kilovolts with a frequency of around one megahertz is applied to the ring electrode (3), generating a largely quadrupolar RF field in the interior. Integrated over time, this RF field produces an effect on confined ions which can be described by a pseudopotential. The pseudopotential has a minimum in the center of the ion trap and increases quadratically in all directions. It thus forms a potential well for the ions, in which they can execute harmonic oscillations around the center or through the center.

The analyte ions were injected into the ion trap through the aperture (4) in the end cap electrode (1). In the ion trap there is a collision gas (usually helium) at a pressure of a few hundredths of a pascal which brings about a damping of the ion oscillations and hence their storage in the center of the ion trap. In the cloud (6) there is an equilibrium between the Coulomb repulsion forces between the ions and the restoring force of the pseudopotential.

The doubly charged analyte ions can then be freed of all other types of ions in the ion trap. This process is called "isolation". It involves ejecting all other types of ion from the ion trap by means of resonant excitation of their oscillations so that only the doubly charged analyte ions remain in the ion trap. The doubly charged analyte ions are also usually the prevalent ions of the analyte substance; at least when the analyte is a peptide and when the ions were generated by electrospray ionization.

The cloud of doubly charged analyte ions is now bombarded with a beam (8) of neutral particles. The neutral particles are generated in an FAB generator (9-14). This requires that ions of a suitable element, here ions of helium, are first generated in a normal electron impact ion source (11) with a thermionic cathode (12) and two guide magnets (13, 14), the helium being introduced into the electron impact ion source (11). The helium ions are extracted in the usual way from the electron impact ion source (11) and accelerated by a voltage difference of a few kilovolts between the housing (11) of the electron impact ion source and the lens system (10). Good electron impact ion sources supply an ion current density of a few $10^{10}$ ions/(s×mm$^2$). The lens system (10) finely focuses the ion beam and sends it through a discharge chamber (9). In this discharge chamber (9) a proportion of the helium ions is discharged by charge stripping with the help of a suitable reaction gas, whereby an electron is transferred from a reaction gas molecule to the helium ion. The discharged helium ions lose practically no kinetic energy in the process and fly on without any deceleration. The beam (8) of neutral particles (in this case, helium atoms) then encounters the cloud (8) of analyte ions and can react with them. The helium ions that are still charged are prevented from entering the ion trap by suitable electric potentials.

Figure 4:
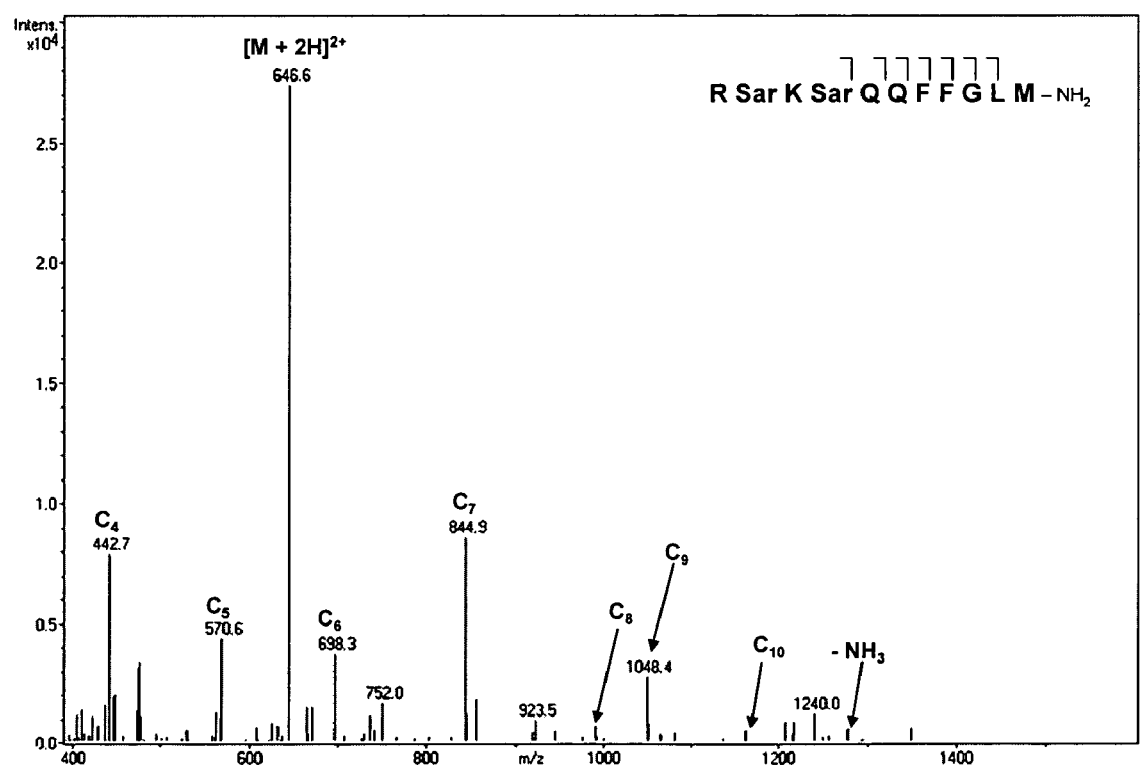
FIG. 4 illustrates a fragment ion spectrum of the $RS_{ar}K$-$S_{ar}QQFFGLM-NH_2$ peptide according to this invention, acquired in a three-dimensional ion trap according to FIG. 1 in a single scan (here still without correct mass calibration and without optimized fragmentation parameters). The fragmentation was brought about by helium atoms with an energy of four kiloelectronvolts, which were admitted into the ion trap for 200 milliseconds.
Figure 5:
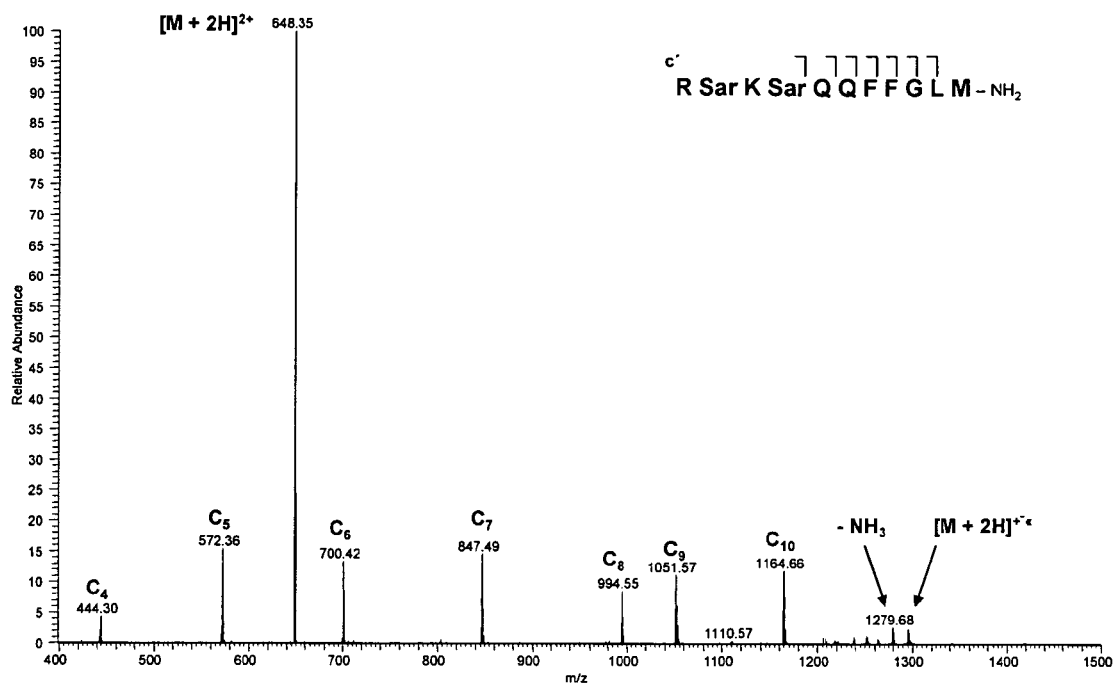
FIG. 5 illustrates an ECD spectrum of the same peptide in an ICR mass spectrometer, obtained by recording and adding 100 scans.
Figure 6:
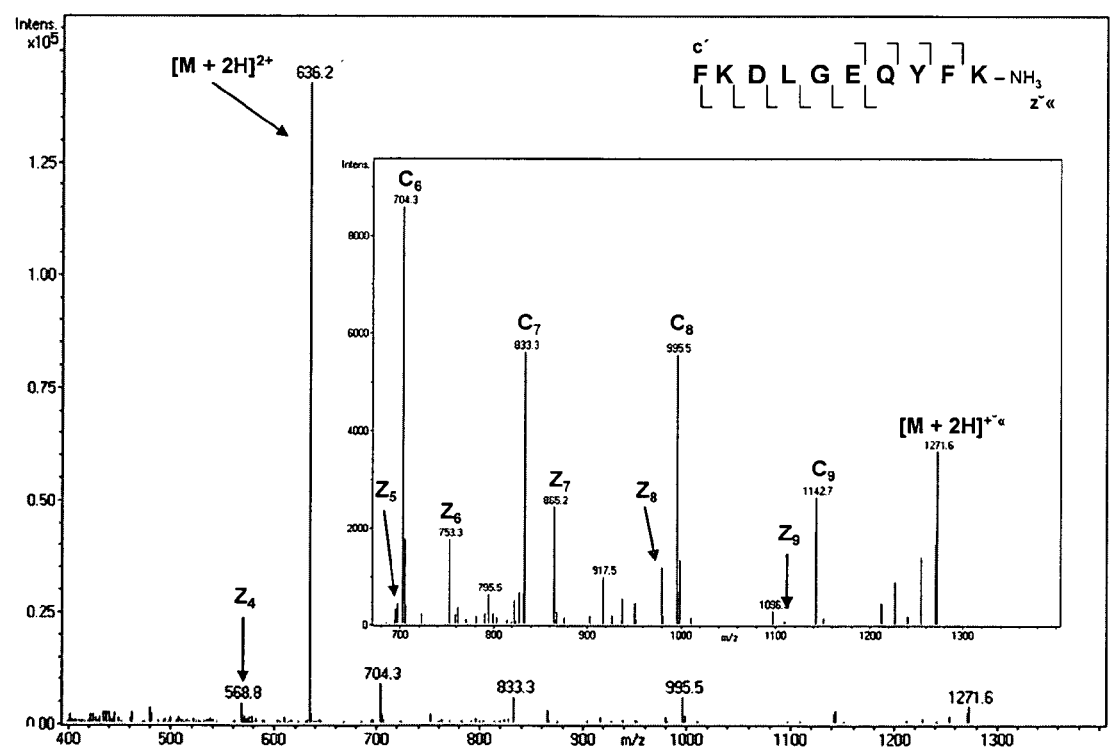
FIG. 6 illustrates a fragment ion spectrum of the $YGA_D$-$FLRRIRPK-NH_2$ peptide according to this invention, analogous to the spectrum of the peptide in FIG. 4.
Figure 7:
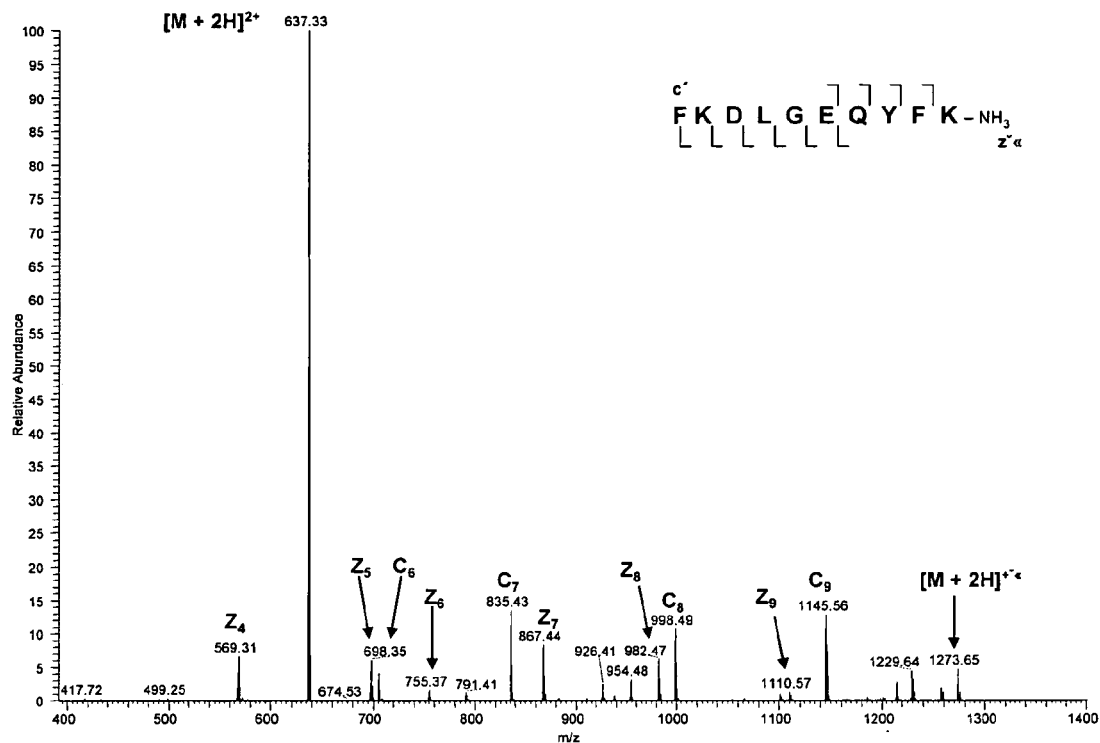
FIG. 7 illustrates an ECD spectrum of the same peptide in an ICR mass spectrometer, again obtained by recording and adding together 100 scans.
Figure 8:
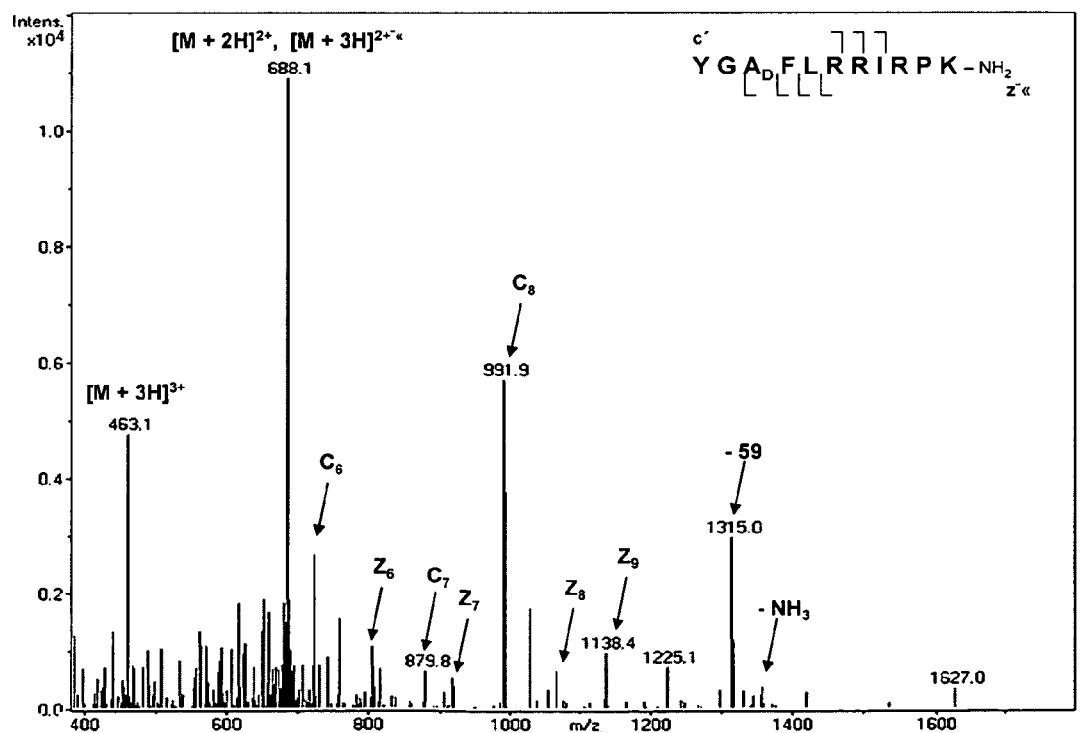
FIG. 8 shows a scan of the fragment ions of the $FKDLGEQYFK-NH_2$ peptide, generated according to this invention in an ion trap from triply charged analyte ions subjected to 200 milliseconds of bombardment with helium atoms of four kiloelectronvolts.
Figure 9:
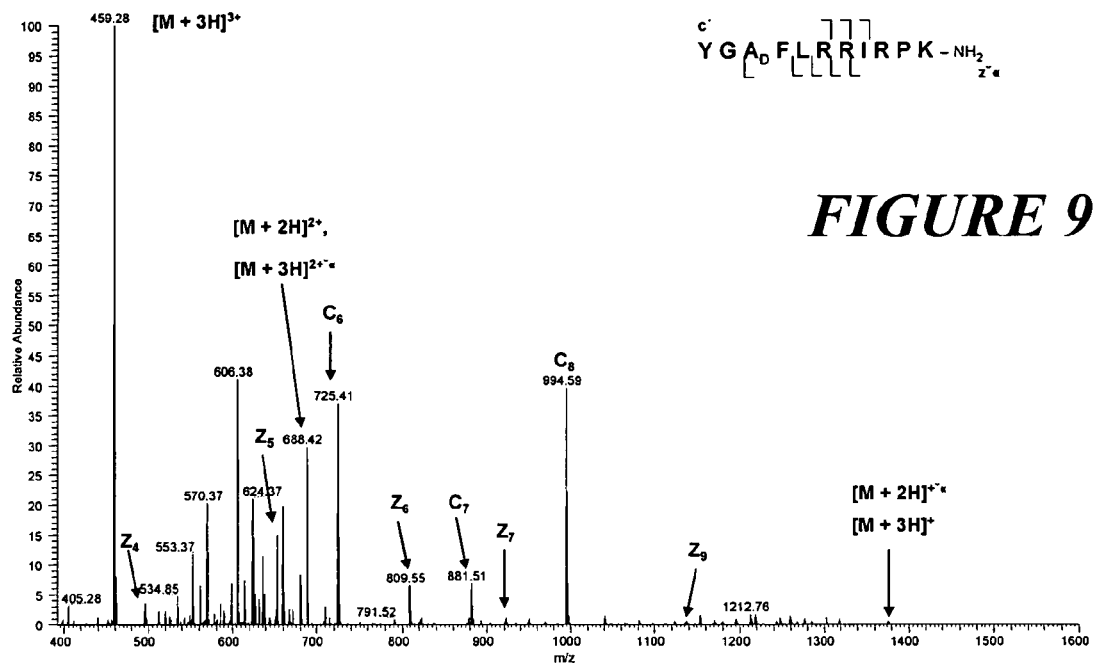
FIG. 9 illustrates an ECD spectrum of the same peptide, also from triply charged analyte ions, obtained from 100 scans in an ICR mass spectrometer.

Results are shown in FIGS. 4, 6 and 8. The spectra are very similar to the ECD spectra in FIGS. 5, 7 and 9, which were acquired in an ICR mass spectrometer. It must be noted that the spectra according to this invention are single scans whereas in the ICR mass spectrometer 100 single spectra are measured and added together. This result is surprising and could not have been expected.

The fragmentation mechanism is still unknown. Years of experience have shown us that a collisionally induced fragmentation CID with formation of B and Y ions occurs when the analyte ions with an energy of around four kiloelectronvolts are injected into a collision gas (which can also be helium). In the reverse case shown in the FIGS. 4, 6 and 8, however, in which the neutral helium atoms with an energy of four kiloelectronvolts are injected into the cloud of analyte ions, this collisionally induced fragmentation CID is not observed. Instead, ions of the C and Z series are formed, just as with ECD. This indicates a new, unknown process about which we can merely speculate here.

Before the experiments began it was expected that either collisionally induced fragmentation or an electronic interaction of the analyte ion with the neutral particle in transit would occur, and the latter should supply A and X ions. This latter case would also represent a fragmentation which was orthogonal to CID. However, the surprising results lead one to suspect, that what we have is a process which involves electron capture or electron transfer. The strong alternating electric field in the ion trap makes it unlikely that the fast helium atoms generate electrons by collisions with the helium damping gas or by impact with the walls of the ion trap, and that these electrons are available for electron capture. These electrons would be ejected from the ion trap within nanoseconds. It could be the case, however, that the helium atoms of the beam of neutral particles are so highly excited that one of the two electrons is extraordinarily weakly bound, so that an electron transfer from a helium atom in transit to an analyte ion can occur. However, this is inconsistent with the fact that, in contrast to electron transfer in reactions with negative ions, the yield here with doubly charged analyte ions is very high. The mechanism therefore needs to be clarified. It must also be noted that a helium atom with four kiloelectronvolts flying past an analyte ion offers roughly the same interaction time as an electron with half an electronvolt of kinetic energy flying past, i.e. an energy which is the best possible for electron capture ECD.

The high excitation could arise as a result of the charge exchange in the discharge chamber (9). In this exchange, the transferred electron remains in a state of high excitation and the excitation energy cannot be emitted. However, the high excitation could also be produced by collisions of the fast helium atoms with the helium atoms of the damping gas in the ion trap.

Figure 2:
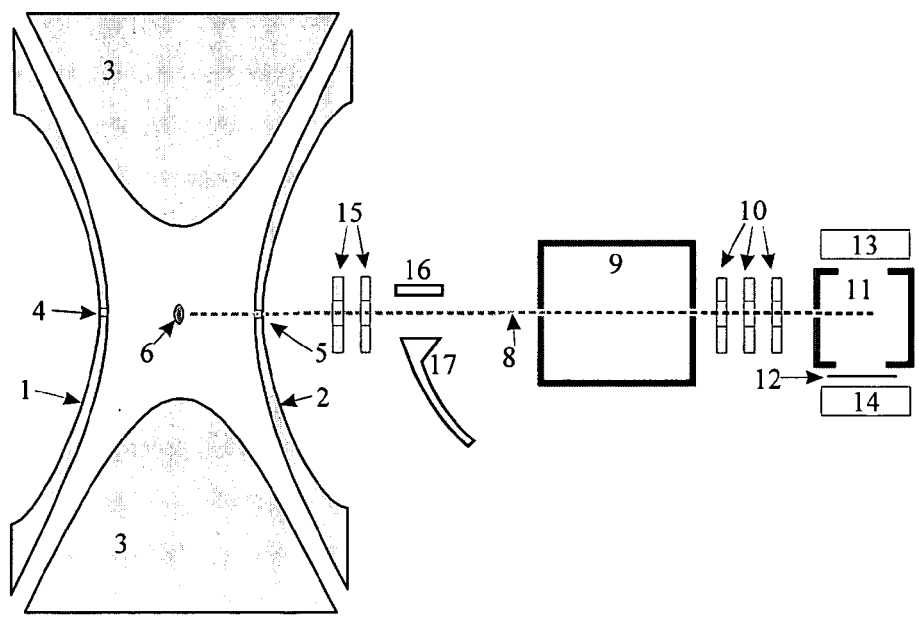
FIG. 2 shows a similar arrangement but with the difference that the beam of neutral particles (8) is injected axially into the ion trap. The beam (8) passes through the detection unit of the mass spectrometer, comprising a conversion dynode (16), which transforms the ions that are mass-selectively ejected from the ion trap through the aperture (5) into electrons, and a channeltron multiplier (17).

FIG. 2 illustrates an arrangement which also allows a bombardment of the ion cloud (6) in the interior of an ion trap (1, 2, 3). It has the advantage that the hole (7) through the ring electrode (FIG. 1) is not required. Instead, use is made of the fact that the arrangement of the detector with conversion dynode (16) and channeltron multiplier (17) makes it possible for the beam (8) of neutral particles to enter the ion cloud (6) through the exit aperture (5).

Figure 3:
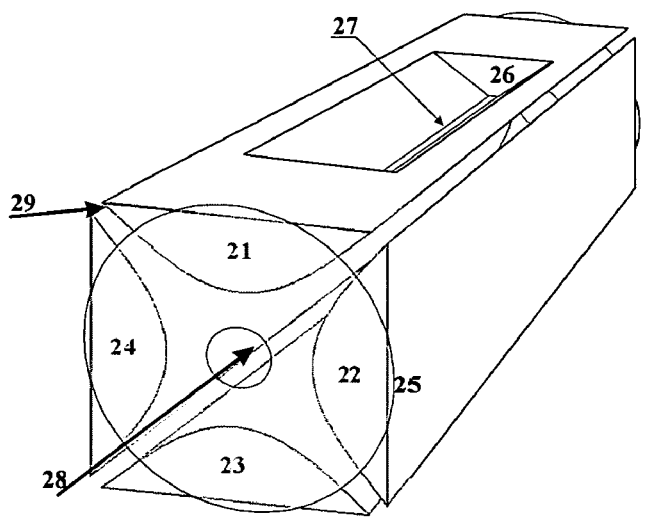
FIG. 3 illustrates a linear ion trap mass spectrometer comprising the four pole rods (21-24), the injection diaphragm (25) at the end surface of the pole rods, and an indentation (26) with a slit (27) for the mass-selective ejection of the ions. The neutral particles can be injected axially as a beam (28), or diagonally as a beam (29) into the open space between the pole rods.

FIG. 3 shows a linear ion trap mass spectrometer. The beam of neutral particles can be injected into the ion trap either axially (28) or diagonally (29) through a slit between the pole rods. For rod-type ion guides—which are basically the same as a linear ion trap, but are generally hexapole or octopole systems, and therefore have more but much thinner rods—it is also possible for the fast neutral particles to penetrate diagonally.

In the case of the spectra in FIGS. 4, 6 and 8, the FAB generator has formed a beam of fast helium atoms with an energy of around four kiloelectronvolts. Commercially available FAB generators usually operate with acceleration voltages of between four and eight kilovolts. It is also possible, however, to operate them in the range of around one to 20 kilovolts. Besides beams of helium atoms, other types of neutral particle beam can be generated in the FAB generators, for example all types of noble gas beams. Moreover, beams of alkali or halogen atoms can also be produced. It does not have to be beams of atoms, however. Beams of molecules can also be produced, for example beams of the diatomic gases oxygen or nitrogen.

The mass spectrum in FIG. 8 was generated from triply protonated ions $(M+3H)^{3+}$. In this process, doubly charged radical cations $(M+3H)^{2+\cdot}$ are also created in considerable numbers by simple electron transfer, but without splitting off a hydrogen atom. As is known from ETD experiments, these doubly charged radical cations can be further split into fragment ions by a gentle excitation with a dipolar alternating excitation voltage, resonantly applied between the two end cap electrodes, resulting in gentle collisionally induced fragmentation. These fragment ions are the same as the ECD fragment ions, i.e. they belong to the C and Z series. This increases the yield of fragment ions yet again. This option, which was not used here for reasons of comparability with corresponding ECD spectra in an ICR mass spectrometer, does not exist in an ICR mass spectrometer, and represents a further advantage of this method in RF ion traps. The number of these radical cations produced in the ICR mass spectrometer is much lower, however.

In FIGS. 1 and 2, the FAB generator (9-14) may be replaced by a generator for a beam of hydrogen radicals (hydrogen in statu nascendi). According to the investigations on the spontaneous fragmentation of analyte ions in MALDI ion sources cited above, it is to be expected that analyte ions are to be split by hydrogen radicals in a similar way. The mechanism, however, is not yet proved. From the cited investigations of in-source decay (ISD) it can be assumed that not only doubly or multiply charged ions are fragmented but also singly charged ions under formation of fragment ions. As in ISD, ECD type ion fragments will be produced in all probability, forming C- and Z-fragment ions. If this is true, then also MALDI ions become available for useful fragmentation. Up to now, MALDI ions are hard to fragment, the fragmentation often covers only parts of the molecule. The only useful kind of fragmentation of MALDI ions is the decay of metastable ions generated in the laser plasma taking place in the drift tube of time-of-flight mass spectrometers. A successful fragmentation process of a second kind would be of high value.

Hydrogen radicals (H') can be generated from hydrogen molecules ($H_2$) by thermic dissociation or by dissociation in a microwave plasma. Such generators for the production of beams of hydrogen radicals are commercially available. The will be used in the fabrication of electronic chips and wafers for purification of surfaces by reduction of pollutions and oxides.

The method of fragmentation by reactions with neutral particles described here can be repeated for all peptides of a mixture, for example a mixture of the digest peptides of a protein, and also compared with the results from collisionally induced fragmentation CID. This produces a very certain identification of the protein. It is even possible to determine differences between the protein analyzed and those in protein sequence databases with certainty. The differences can be of the mutative type or modifications of the protein originally produced in a cell with the help of a DNA code.

The fragmentation by neutral particles made possible by the invention has a further advantage which is not immediately apparent. The fragmentation at low RF voltage means that all daughter ions down to low masses can be stored because the threshold mass is now very low. An ion trap can only store ions above the threshold mass, which is proportional to the RF voltage. Up to now it was not possible to store small daughter ions because collisionally induced fragmentation CID required a minimum RF voltage, below which the collision energy was too small and a fragmentation was often not possible. Only by using very low RF voltages is it possible to scan the complete amino acid fragment spectrum of the C cleavages, starting from the first amino acid. Example: A large doubly charged peptide with 20 amino acids has a molecular weight of around 2400 atomic mass units and a specific mass of m/z=1200 mass units per elementary charge. Normally, daughter ions produced by collisionally induced fragmentation can only be stored above a threshold mass of some 400 mass units per elementary charge (corresponding to around three to four amino acids). But now, by selecting a very low RF voltage, it is possible to achieve storage from 55 mass units per elementary charge upwards, so that even the smallest terminal amino acid can still be collected.

The invention cannot only be used in ion trap mass spectrometers, instead, it can be used in almost any type of mass spectrometer. A particularly interesting type of mass spectrometer is the time-of-flight mass spectrometer with orthogonal ion injection (OTOF), as shown in FIG. 10.

Figure 10:
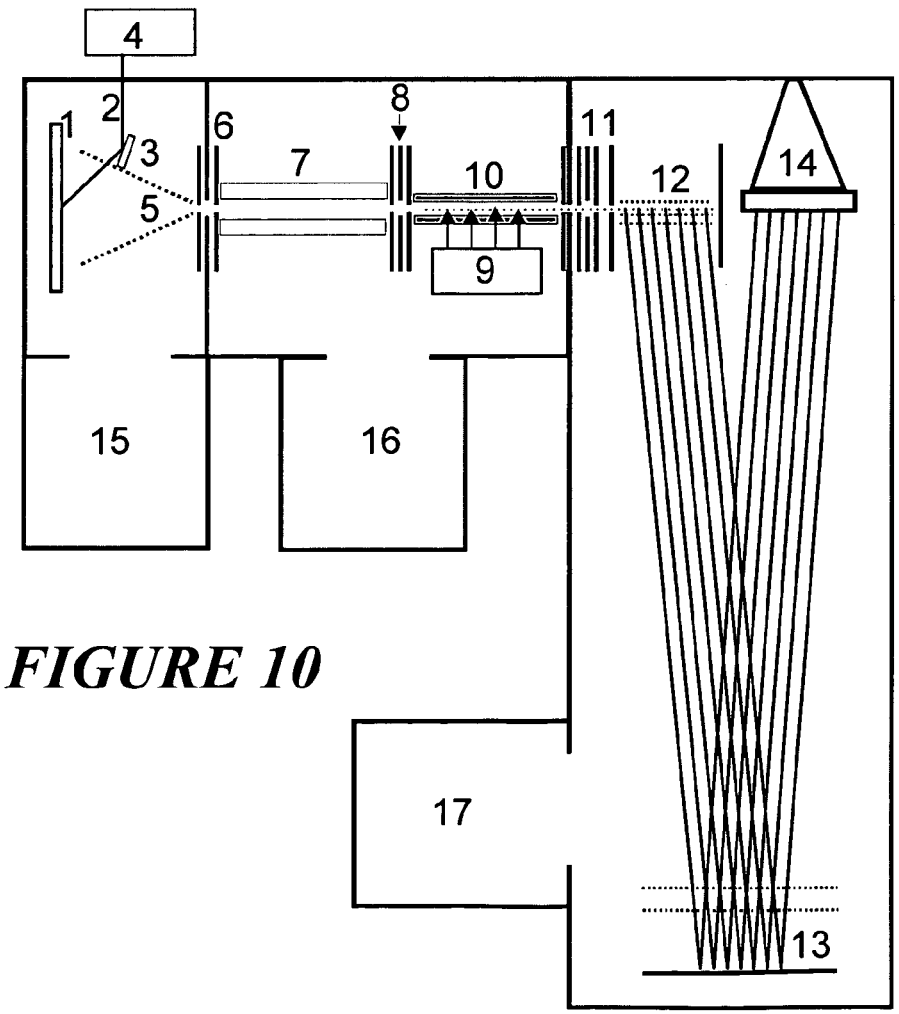
FIG. 10 presents a schematic view of a time-of-flight mass spectrometer with orthogonal injection of ions (OTOF), operated with a MALDI ion source. A laser beam (2) from a laser (4) irradiates a sample on a sample support plate (1) and generates ions. Suitable parent ions will be filtered in a selection stage (7), fragmentation will be induced by reactions of hydrogen radicals in a reaction chamber (10).

As shown schematically in FIG. 10, this spectrometer not only can (as many others) used with an electro spray ion source (ESI), but also with ionization by matrix-assisted laser desorption (MALDI). The sample on the sample support plate (1) are irradiated by a pulsed beam of light (2) via a mirror (3) from a pulse laser (4). The ions generated in the desorption plasma will be collected by an ion funnel (5) and guided through a stack of apertures (6) into a quadrupole filter (7) for selection of the chosen type of parent ions. The selected parent ions will be fed through a further stack of apertured diaphragms (8) into the fragmentation chamber, where the parent ions react with hydrogen radicals with formation of fragment ions. These fragment ions are slightly accelerated through lens system (11) into the pulser (12) of the time-of-flight mass analyzer. Here the ions are pulsed vertically into the drift tube, reflected in the reflector (13), and measured by the ion detector (14). The mass spectrometer is pumped by a differential pumping system consisting of several pumps (15), (16), and (17).

Such a time-of-flight mass spectrometer has several advantages: high mass resolution, high mass accuracy, high dynamic measuring range. It is best suited for the new fragmentation methods of the invention.

Other advantages will become evident as a result of further clarification of the processes involved. It therefore appears quite feasible that further orthogonal fragmentation processes can be achieved with other neutral particle energies or other types of neutral particle, for example those which, as described above, lead to A and X cleavages. These and other fragmentation mechanisms are intended to be included in the basic idea of the invention.

What is claimed is:

1. Method for the fragmentation of analyte ions, wherein the analyte ions are fragmented by reactions with electronically excited or radical neutral particles.

2. Method according to claim 1, wherein a cloud of analyte ions is bombarded by a beam of electronically excited or radical neutral particles.

3. Method according to claim 2, wherein the cloud of analyte ions is kept in an ion trap.

4. Method according to claim 3, wherein the ion trap is a magnetic ion trap, a linear RF ion trap or a three-dimensional RF ion trap.

5. Method according to claim 3, wherein only selected types of ions are to be stored in the ion trap for the bombardment with neutral particles.

6. Method according to claim 2, wherein the cloud of analyte ions is located in an ion guide during the bombardment with neutral particles.

7. Method according to claim 2, wherein at least some of the analyte ions of the cloud are multiply charged.

8. Method according to claim 7, wherein the analyte ions of the cloud are doubly charged.

9. Method according to claim 2, wherein the beam of electronically excited neutral particles for the bombardment of the cloud of analyte ions is generated in a conventional FAB generator.

10. Method according to claim 9, wherein the electronically excited neutral particles have kinetic energies between one and twenty kiloelectronvolts.

11. Method according to claim 2, wherein electronically excited noble gas atoms, excited alkali atoms or excited halogen atoms are used as neutral particles.

12. Method according to claim 11, wherein electronically excited helium atoms are used as neutral particles.

13. Method according to claim 2, wherein electronically excited atoms or electronically excited molecules of oxygen or nitrogen are used as neutral particles.

14. Method according to claim 2, wherein hydrogen radicals are used as neutral particles.

15. Mass spectrometer for the acquisition of fragment ion spectra of an analyte substance, comprising
   a) an ion storage or guiding device to store or guide the analyte ions, and
   b) a generator to generate a beam of electronically excited or radical neutral particles which can be injected into the ion storage or guiding device.

16. Mass spectrometer according to claim 15, wherein the ion storage device is a magnetic ion trap, a linear RF ion trap or a three-dimensional RF ion trap.

17. Mass spectrometer according to claim 15, wherein the generator for the generation of the beam of neutral particles is an FAB generator.

18. Mass spectrometer according to claim 15, wherein the generator for the generation of the beam of radical neutral particles is a generator delivering a beam of hydrogen radicals.

19. Mass spectrometer according to claim 15, wherein the mass spectrometer comprises means to select and isolate singly, doubly or multiply charged ions of the analyte substance.

20. Method according to claim 1, wherein electronically excited or radical neutral particles are bombarded by a beam of analyte ions.

21. Method according to one of claim 20, wherein at least some of the analyte ions are singly charged.

22. Method according to one of claim 2, wherein at least some of the analyte ions are singly charged.

23. Method according to claim 1, wherein the analyte ions are additionally collisionally excited.

24. Method according to claim 1, wherein the electronically excited neutral particles are metastable.

* * * * *